United States Patent [19]

Vaguine

[11] Patent Number: 4,589,424
[45] Date of Patent: May 20, 1986

[54] MICROWAVE HYPERTHERMIA APPLICATOR WITH VARIABLE RADIATION PATTERN

[75] Inventor: Victor A. Vaguine, Dallas, Tex.

[73] Assignee: Varian Associates, Inc, Palo Alto, Calif.

[21] Appl. No.: 525,182

[22] Filed: Aug. 22, 1983

[51] Int. Cl.$^4$ .............................................. A61N 5/02
[52] U.S. Cl. .............................. 128/804; 219/10.55 F
[58] Field of Search .............. 128/804, 802, 399, 401; 219/10.55 R, 10.55 A, 10.55 F

[56] References Cited

U.S. PATENT DOCUMENTS

| | | | |
|---|---|---|---|
| 2,388,830 | 11/1945 | Cotton | 128/804 X |
| 3,783,221 | 1/1974 | Soulier | 219/10.55 A |
| 4,108,147 | 8/1978 | Kantor | 128/404 |
| 4,316,474 | 2/1982 | Spethmann | 128/804 |
| 4,462,412 | 7/1984 | Turner | 128/804 |

FOREIGN PATENT DOCUMENTS 537765  7/1941  United Kingdom ................ 128/804

OTHER PUBLICATIONS

A. Y. Cheung et al, "Direct Contact Applicators for Microwave Hyperthermia,", *J. Microwave Power,* 16(2), 1981, p. 151.

G. Kantor, "Evaluation and Survey of Microwave and Radiofrequency Applicators,", *J. Microwave Power,* 16(2), 1981, p. 135.

P. F. Turner, "Deep Heating of Cylindrical or Elliptical Tissue Masses," Third Int. Symposium: Cancer Therapy by Hyperthermia, Drugs, and Radiation, Fort Collins, Colorado, Jun. 22-26, 1980.

D. A. Christensen, "A New Non-Perturbing Temperature Probe Using Semiconductor Band Edge Shift," *J. Bioengineering,* vol. 1, pp. 541-545, 1977.

D. A. Christensen et al, "Hyperthermia Production for Cancer Therapy: A Review of Fundamentals and Methods," *J. Microwave Power,* 16(2), 1981, p. 89.

V. A. Vaguine et al, "Microwave Direct-Contact Applicator System for Hyperthermia Therapy Research," Third Int. Symposium: Cancer Therapy by Hyperthermia, Drugs, and Radiation, Ft. Collins, Colorado, Jun. 22-26, 1980.

*Primary Examiner*—Lee S. Cohen
*Attorney, Agent, or Firm*—Stanley Z. Cole; William R. McClellan; Kenneth L. Warsh

[57] ABSTRACT

A direct contact microwave hyperthermia applicator includes a plurality of rectangular waveguide sections each having a radiating aperture. The waveguide sections are mounted with their long sides abutting. A pair of shutter elements for individually varying the radiating aperture is associated with each of the waveguide sections. The shutters can be adjusted to form a desired composite aperture which produces a radiation pattern adapted for efficient hyperthermia treatment of a tumor having a prescribed size, shape and location. Microwave power supplied to the radiating elements can be varied in phase and power level to further control the radiation pattern.

4 Claims, 2 Drawing Figures

MICROWAVE HYPERTHERMIA APPLICATOR WITH VARIABLE RADIATION PATTERN

BACKGROUND OF THE INVENTION

This invention relates to hyperthermia treatment of tissue by irradiation with microwave energy and, more particularly, to an novel microwave applicator having a variable radiation pattern.

Hyperthermia has received a great deal of attention in recent years as a form of cancer therapy. In hyperthermia, the temperature of a tumor is typically raised to the range of 42° C. to 45° C. Such temperatures can kill both malignant and normal cells. Hyperthermia is made practical by selective heating of tumors, either alone or in conjunction with chemotherapy or radiation therapy. Microwave energy has been used to provide hyperthermia treatment. The microwave energy is applied to malignant tissue by an applicator, which acts as an antenna, and is coverted to heat in the tissue. Both external, or surface, applicators and implantable applicators have been used. However, surface applicators are preferable from a convenience standpoint.

Significant problems have been encountered in selectively heating malignant tumors to the required temperature without overheating the surrounding normal tissue. Individual rectangular and circular waveguide sections having radiating apertures have been utilized for microwave hyperthermia treatment. See, for example, A. Y. Cheung et al, "Direct Contact Applicators for Microwave Hyperthermia," *J. Microwave Power*, 16(2), 1981, p. 151 and G. Kantor, "Evaluation and Survey of Microwave and Radiofrequency Applicators, " *J. Microwave Power*, 16(2), 1981, p. 135. However, individual microwave applicators are not effective in treatment of deep-seated tumors. Frequencies above about 500 MHz are rapidly attenuated in tissue and do not produce substantial heating at depths beyond about 1 or 2 cm. Lower frequencies experience less attenuation in tissue but cannot be focused with practical sized applicators.

This problem has been alleviated to some extent by the use of multiple applicators directed at a tumor from different directions resulting in an increased power level in the region where the radiation patterns intersect. The incident radiation can be incoherent or can be phase controlled to provide a phased array antenna. P. F. Turner in "Deep Heating of Cylindrical or Elliptical Tissue Masses," Third International Symposium: Cancer Therapy by Hyperthermia, Drugs, and Radiation, Fort Collins, Col. June 22–26, 1980, describes an annular phased array for hyperthermia treatment. The radiating apertures have fixed positions around a central opening in which the patient is located. Such applicator systems are large and expensive and require precise positioning of the patient. Furthermore, since the system is spaced apart from the patient, higher power levels are required to achieve the same amount of heating, and the danger associated with leakage of microwave power is increased.

Malignant tumors can be located virtually anywhere in the human body, ranging from the skin surface to deep-seated organs. Furthermore, the tumors can have virtually any size and shape. It is desirable to provide a microwave hyperthermia applicator which can effectively treat tumors regardless of their size, shape or location. Heretofore, microwave applicators have had a fixed configuration and, therefore, have lacked this flexibility.

It is a general object of the present invention to provide a novel microwave hyperthermia applicator.

It is another object of the present invention to provide a microwave hyperthermia applicator with a variable radiation pattern.

It is yet another object of the present invention to provide a microwave hyperthermia applicator capable of treating a variety of tumor locations, sizes and shapes.

SUMMARY OF THE INVENTION

According to the present invention, these and other objects and advantages are achieved in an applicator for hyperthermia treatment of tissue by irradiation with microwave energy. The applicator comprises a plurality of microwave radiating elements each including a microwave radiating aperture. The radiating elements are positioned to form an array of radiating apertures. A variable shutter means is associated with each of the radiating elements for individually varying the radiating apertures and forming a desired composite aperture. The applicator further includes means for coupling each of the radiating elements to a microwave power source. The shutter means can be adjusted to provide a radiation pattern adapted for efficient hyperthermia treatment of tissue having a prescribed size, shape and location. The radiating elements are typically rectangular waveguide sections. The microwave signal supplied to the radiating elements can be varied in amplitude and phase to control the radiation pattern.

BRIEF DESCRIPTION OF THE DRAWINGS

For a better understanding of the present invention, together with other and further objects, advantages and capabilities thereof, reference may be had to the accompanying drawings which are incorporated herein by reference and in which.

DETAILED DESCRIPTION OF THE INVENTION

Figure 1:
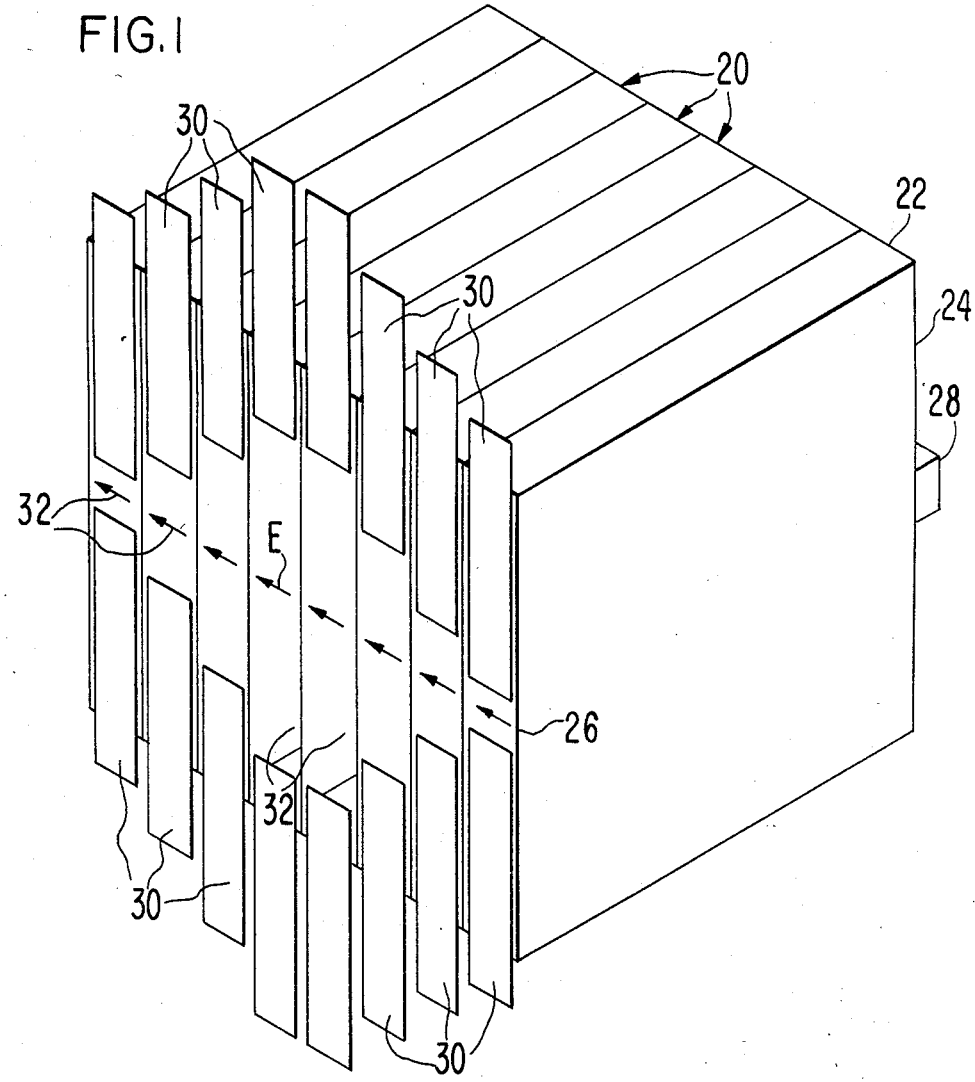
FIG. 1 is a perspective view of a microwave hyperthermia applicator in accordance with the present invention.

A preferred embodiment of an applicator in accordance with the present invention is illustrated in FIG. 1. The applicator includes a plurality of rectangular waveguide sections 20 mounted side-by-side and operated in the $TM_{01}$ mode. Each of the waveguide sections 20 has a rectangular cross-section including a short side 22 and a long side 24. The waveguide sections 20 each include an open end 26 and are mounted together with their long sides 24 abutting. The opposite end of each of the sections 20 is closed and includes a connector 28 or other means for coupling microwave energy into the waveguide section. The use of individual rectangular waveguide sections is described in A. Y. Cheung et al, *J. Microwave Power*, 16(2), 1981, p. 151, and in G. Kantor, *J. Microwave Power*, 16(2), 1981, p. 135. The waveguide sections 20 can be air-filled or can be partially or completely filled with dielectric material to permit operation at lower frequencies.

The open end 26 of each of the waveguide sections 20 is provided with a pair of movable shutter elements 30 which are slidable in the plane of the open end 26 and are operative to partially or completely close off the open end 26. The portion of the open end 26 not closed off by the shutter elements 30 emits microwave radiation and acts as a radiating aperture 32, the dimension of which is controlled by the positions of the shutter elements 30. The configuration of the waveguide sections 20 provides aligned electric fields at the radiating apertures 32 and a linearly polarized radiation field. The shutter elements 30 can be thin metal strips which are slidable in grooves 34 (FIG. 2) provided along the edges of the open ends 26. Shutter elements 30 of different lengths can be provided, and the ends adjacent the aperture 32 can be cut at an angle or with a curve in order to further shape the aperture. By adjustment of the shutter elements 30 on each of the waveguide sections 20, a composite aperture comprising the radiating apertures 32 and having a prescribed size and shape is formed. The shutter elements 30 can be completely removed to permit the full use of the open end 26 of the waveguide section 20 as a radiating aperture.

In the applicator of FIG. 1, the individual waveguide sections, or radiating elements, are mounted in abutting relationship with coplanar radiating apertures 32. It is to be understood that radiating elements can be separated or can be mounted at angles so that the radiating apertures lie on a contoured surface. A contoured arrangement of radiating apertures is useful in matching the applicator to the contour of the body section under treatment. Individual apertures can be curved by imparting a curve to the open end of the waveguide sections. Furthermore, the cross-section of the waveguide sections is not necessarily rectangular.

Figure 2:
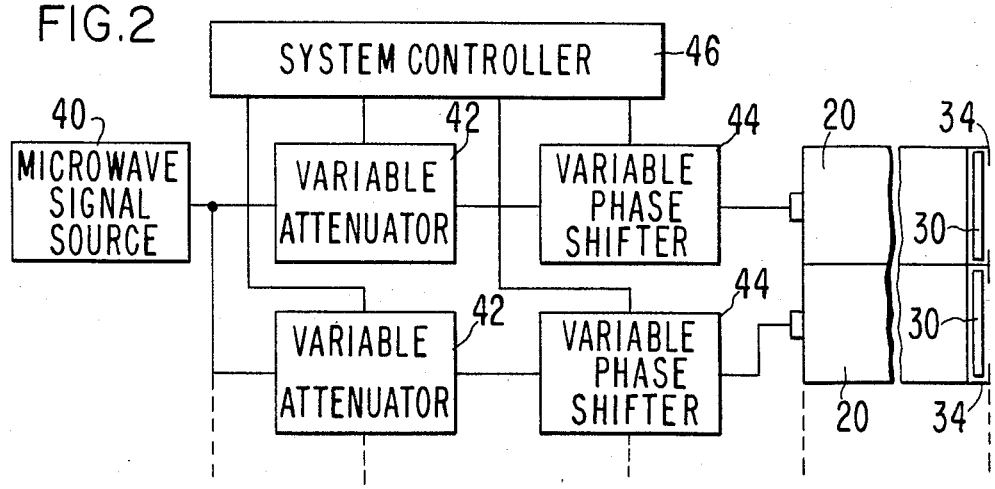
FIG. 2 is a partial block diagram of a hyperthermia treatment system in accordance with the present invention.

A partial block diagram of a hyperthermia treatment system utilizing the applicator shown in FIG. 1 is illustrated in FIG. 2. The waveguide sections 20, two of which are shown schematically in FIG. 2, receive microwave energy from a microwave signal source 40 which is typically in the frequency range between 200 MHz and 3,000 MHz. The output of the source 40 is coupled through a microwave power divider and through variable attenuators 42 and variable phase shifters 44 to each of the waveguide sections 20. Thus, the power level and the phase of the microwave energy supplied to each waveguide section 20 is individually controllable. Preferably, the variable attenuators 42 and the variable phase shifters 44 are controlled by a system controller 46, in response to inputs from an operator to provide the desired radiation pattern and power level.

In operation, the size, location and shape of the tumor being treated are determined. From this information, a suitable radiation pattern and power level can be determined. Each of the shutter elements 30 is individually adjusted to provide a composite aperture size and shape suited for treatment of the tumor. By adjusting the variable phase shifters 44 to provide a known phase relationship between the microwave signals supplied to each of the waveguide sections 20, the radiation pattern can be shaped and can be focused at a prescribed depth and in a prescribed direction. Furthermore, by varying the phase relationship of the excitation signals during treatment, the radiation pattern can be scanned over a prescribed area. The variable attenuators 42 control the level of the microwave energy provided to each of the waveguide sections 20. While the applicator, in accordance with the present invention, is considered a direct contact applicator, the treatment is typically applied to a patient through a cooling fluid such as water contained in a flexible rubber enclosure. The water cools the surface of the tissue being treated and improves impedance matching between the applicator and the tissue, thereby reducing reflection of microwave energy from the tissue surface. During treatment, the temperature of the tissue is monitored by temperature sensors (not shown) positioned on the skin and at various locations in or near the tumor under treatment. The temperature sensors can be thermistors, thermocouples or, preferably, optical temperature sensors. Optical temperature sensors are described by D. A. Christiansen in "A New Non-Perturbing Temperature Probe Using Semiconductor Band Edge Shift," *J. Bioengineering*, Vol. 1, pp. 541–545, 1977. If a predetermined maximum temperature is exceeded, the power supplied to the applicator can be reduced or shut off. The treatment is applied for a predetermined time, typically in the range of one-half hour to one hour.

While there has been shown and described what is at present considered the preferred embodiments of the invention, it will be obvious to those skilled in the art that various changes and modifications may be made therein without departing from the scope of the invention as defined by the appended claims.

I claim:

1. An applicator for hyperthermia treatment of tissue by irradiation with microwave energy comprising:
   a plurality of side-by-side rectangular waveguides each having an open end forming a radiation aperture, whereby apertures of said plurality of waveguides provide a composite radiation aperture;
   variable shutter means associated with each of said radiation apertues for individually varying said radiation apertures and forming a desired shape for said composite aperture, said shutter means comprising two shutter elements associated with each of said apertures and slidable across each said aperture, the two shutters for individual ones of said apertures being moveable toward and away from each other, the shutters for adjacent ones of said apertures being moveable along paths which are parallel one to the other; and
   means for coupling each of said waveguides to a microwave power source,
   whereby said shutter means can be adjusted to provide a radiation pattern adapted for efficient hyperthermia treatment of tissue having a prescribed size, shape and location.

2. The applicator as defined in claim 1 wherein said waveguides are arranged with coplanar radiating apertures.

3. The applicator as defined in claim 1 wherein each of said waveguides are elongated in cross-section and are arranged so that the longer sides thereof are side-by-side.

4. The applicator as defined in claim 1 wherein each of said waveguides is at least partially filled with dielectric material to permit operation at lower frequencies.

* * * * *